Nov. 17, 1964 D. WALKER ETAL Plant Pat. 2,452
GLADIOLUS PLANT
Filed Dec. 27, 1962
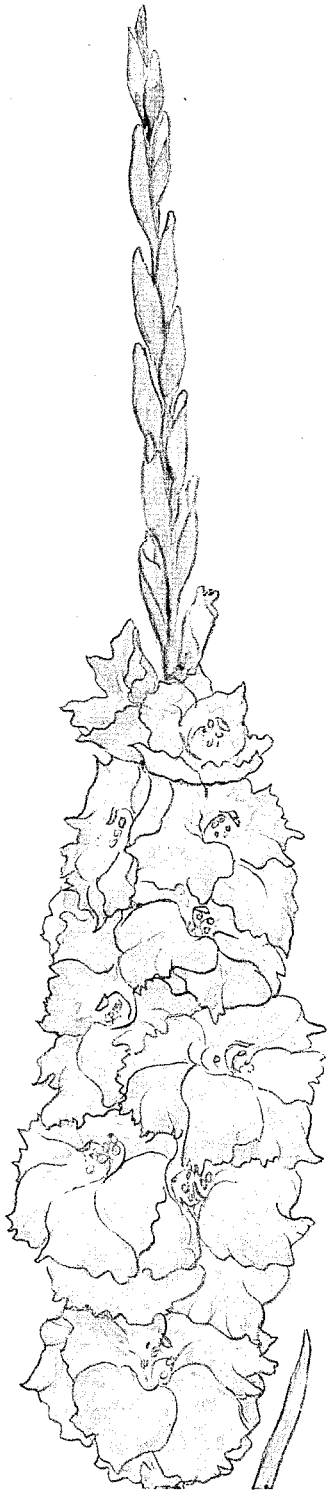
INVENTORS
DON WALKER AND
BY AUDREY WALKER
Kleinberg & Lilling
ATTORNEYS United States Patent Office Plant Pat. 2,452
Patented Nov. 17, 1964

2,452
GLADIOLUS PLANT

Don Walker and Audrey Walker, both of
323 Aquetong Road, New Hope, Pa.

Filed Dec. 27, 1962, Ser. No. 247,777
1 Claim. (Cl. Plt.—85)

Our new invention relates to a new and distinct variety of gladiolus plant.

The outstanding characteristic of our new gladiolus plant is its true lavender color.

The new variety grows straight and does not crook or twist under any conditions. It produces nine or eleven leaves instead of the customary seven.

We have asexually reproduced the new variety by cormels through several generations in New Hope, Pennsylvania, and established that the characteristics and distinctions of the variety are true and are transmitted through succeeding propagations.

The drawing shows a typical specimen of a flower spike of the new variety, with the flowers in varied stages of growth. Some are shown as closed buds, others as partially opened buds, and others as fully opened flowers. The colors depicted are as nearly true as is possible in this type of reproduction.

The following is a detailed description of the new variety.

The variety was first observed and grown in New Hope, Pennsylvania.

Succeeding generations have established that the distinguishing characteristics of the variety hold true through propagations by plantings derived from cormels.

*The Plant*

*Growth habits.*—Similar to those of its parents, but a little more vigorous and prolific. The blossom spike attains an average height of sixty inches under normal cultural conditions.

*Blooming habit.*—If planted in the middle Atlantic States of the United States during the spring months it comes into bloom in about 85 to 90 days from the planting of large corms. This blooming habit is usually referred to as "medium-late."

*Stems.*—The stems are exceptionally tall and straight. Freedom from crooking is one of the features of this variety. The diameter of the stem just above the corm is approximately three-quarters of an inch. At that point, the stems are deep rose in color, which pigment gradually lightens, blending into green as ground level is approached, where all rose color disappears.

*Foliage.*—The foliage of the variety is in a true fan-shape with the flower spike emerging in the center of the fan. From 9 to 11 leaves are produced as opposed to the usual 7 leaves on a gladiolus plant. The tallest leaves are in the middle of the fan, and under normal culture will reach a height of 36 inches with a base width of 2 inches, tapering gradually to the tip. The foliage is green in color.

*Disease resistance.*—The variety has been found to be unusually resistant to the usual gladiolus plant diseases of a bacterial or fungoid genesis, including Fusarium, Septoria, and Sclerotinia.

*Corms.*—The new variety produces larger than average corms. They are high-crowned and covered with a heavy husk which is of a medium tan color with a flush of rose. Near the top of the corm there is some light brown vertical striping. The color of the corm flesh is creamy yellow. The exact corm size depends upon the size of the stock from which the corm was grown, but it is generally larger than those of most other varieties of gladiolus plant.

*The Flower*

*Spike.*—The spike is tall and regularly opens 8 to 10 buds before the bottom floret breaks down. The average flowerhead under normal conditions grows to at least 28 inches.

*Bud.*—The average bud is about 3 to 3½ inches in length when opening. The length of the buds diminishes naturally in size towards the tip of the flower spike.

*Flower.*—The flowerhead of the new variety has a formal placement wherein all florets face forward and there is no vertical separation between them. The individual florets average about 5 inches in diameter at the bottom of the flowerhead, and decrease in size progressively approaching the tip. The florets are somewhat triangular, wide-open and ruffled. The flowers keep well.

*Petals.*—The petals are also somewhat triangular and ruffled (not needle-pointed). The petals have heavy substance and texture. The upper petals are approximately 2 inches wide and the lip petals are approximately 1 and ½ inches wide. The flower has no fragrance. The petals of the variety, by reference to the Horticultural Color Charts issued by the British Color Council, are sea-lavender violet, Plate 637/2, with a cleanly marked throat of white. Unopened buds showing color have an edge of sea-lavender violet, Plate 637/1.

*Reproductive Organs*

*Stamens.*—The stamens are white and are marked underneath with two longitudinal stripes of sea-lavender violet, Plate 637.

*Pistil.*—The pistil is pure white in color.

The new variety was obtained by crossing two gladiolus varieties, to wit, Sir Galahad and Caribbean.

Study of the new variety by plant geneticists reveals that certain specific chromosomes of the new variety are doubled, thereby making this variety truly unique.

Additionally, the new variety has a hollow stem which makes it admirably suitable for shipping. It refrigerates well and its flowers will open in a satisfactory manner after the stem is trimmed and placed in water.

The parents of the new variety are registered with the North American Gladiolus Registry published in Sardinia, New York.

Having thus described our invention and illustrated its use, what we claim as new and desire to secure by Letters Patent is:

A new and distinct variety of gladiolus plant, substantially as herein shown and described, characterized by its true lavender color and its 9 to 11 leaves.

No references cited.